(12) United States Patent
Bonitati (10) Patent No.: US 8,721,733 B2
(45) Date of Patent: May 13, 2014

(54) PROSTHESIS KIT WITH FINNED SLEEVE

(75) Inventor: John A Bonitati, Warsaw, IN (US)

(73) Assignee: Depuy (Ireland), Cork (IE)

( * ) Notice: Subject to any disclaimer, the term of this patent is extended or adjusted under 35 U.S.C. 154(b) by 0 days.

(21) Appl. No.: 13/470,415

(22) Filed: May 14, 2012

(65) Prior Publication Data

US 2013/0304220 A1 Nov. 14, 2013

(51) Int. Cl.
*A61F 2/30* (2006.01)
*A61F 2/38* (2006.01)

(52) U.S. Cl.
USPC .......... 623/23.46; 623/23.24; 623/23.21; 623/20.34

(58) Field of Classification Search
USPC .......... 623/23.21–23.35, 23.46, 23.52, 623/20.14–20.17, 20.2–20.36, 23.18
See application file for complete search history.

(56) References Cited

U.S. PATENT DOCUMENTS

| 4,634,444 | A | | 1/1987 | Noiles | |
|---|---|---|---|---|---|
| 4,790,852 | A | | 12/1988 | Noiles | |
| 4,908,036 | A | * | 3/1990 | Link et al. | 623/23.22 |
| 4,944,759 | A | * | 7/1990 | Mallory et al. | 623/22.31 |
| 5,540,694 | A | | 7/1996 | DeCarlo, Jr. | |
| 5,782,921 | A | | 7/1998 | Colleran | |
| 5,824,097 | A | | 10/1998 | Gabriel | |
| 5,906,644 | A | | 5/1999 | Powell | |
| 6,010,534 | A | * | 1/2000 | O'Neil et al. | 623/20.34 |
| 6,171,342 | B1 | | 1/2001 | O'Neil | |
| 6,264,699 | B1 | | 7/2001 | Noiles | |
| 7,044,975 | B2 | * | 5/2006 | Cheal et al. | 623/22.42 |
| 7,291,174 | B2 | | 11/2007 | German | |
| 7,799,085 | B2 | * | 9/2010 | Goodfried et al. | 623/20.15 |
| 2003/0171756 | A1 | | 9/2003 | Fallin | |
| 2003/0204267 | A1 | | 10/2003 | Hazebrouck | |
| 2004/0153081 | A1 | | 8/2004 | Tulkis | |
| 2005/0107883 | A1 | | 5/2005 | Goodfried | |
| 2006/0030945 | A1 | | 2/2006 | Wright | |
| 2010/0076565 | A1 | | 3/2010 | Thomas | |
| 2010/0114323 | A1 | * | 5/2010 | Deruntz et al. | 623/20.21 |
| 2012/0016482 | A1 | | 1/2012 | Mooradian et al. | |

FOREIGN PATENT DOCUMENTS

| EP | 980679 A2 | 2/2000 |
|---|---|---|
| WO | WO 2006127486 A2 | 11/2006 |

OTHER PUBLICATIONS

European Search Report for Corresponding App. No. 09174094.4 Dated Jan. 8, 2010, 8 Pages.
European Search Report for Corresponding App. No. 09174095.1 Dated Jan. 13, 2010, 8 Pages.

(Continued)

*Primary Examiner* — Thomas J Sweet
*Assistant Examiner* — Cheryl Miller (57) ABSTRACT

A modular prosthesis kit includes a sleeve. The sleeve has a central portion and a fin. At least part of the central portion includes a plurality of adjacent terraces. The fin includes a pair of tapered outer surfaces that are continuous, non-terraced and define a wedge-shape to stabilize the position of the sleeve when implanted. The sleeve may include a single terraced spout or wing with such a fin or may not have any spouts or wings extending out from the central portion. The kit may also include sleeves with two spouts or wings extending out from the central portion.

14 Claims, 9 Drawing Sheets

(56) References Cited

OTHER PUBLICATIONS

European Search Report for Corresponding App. No. 11190113.8-2310 Dated Jan. 16, 2012, 8 Pages.
Knee Revision Portfolio, Depuy Orthopaedics, Inc., 2008, 0612-00-506 (Rev. 2), 28 Pages.
LCS Complete Knee Revision Surgical Technique, Depuy Orthopaedics, Inc., 2010, 0612-00-508 (Rev. 2), 60 Pages.
Revision Knees Addressing Instability With Metaphyseal Sleeves, Depuy Orthopaedics, Inc., 2010, 0612-20-510, 2 Pages.
S-ROM Modular Hip System Design Rationale, Depuy Orthopaedics, Inc., 2005, 0612-10-503, 12 Pages.
S-ROM Modular Hip System, Minimally Invasive Calcar Miller Surgical Technique, Depuy Orthopaedics, Inc., 2004, 0612-04-503, 12 Pages.
S-ROM Noiles Rotating Hinge Surgical Technique, Depuy Orthopaedics, Inc., 2011, 0612-85-510 (Rev. 1), 64 Pages.
Sigma Revision and M.B.T. Revision Tray Surgical Technique, Depuy Orthopaedics, Inc., 2008, 0612-51-506 (Rev. 1), 82 Pages.
Stemless Revision TKA Utilizing Metaphyseal Press Fit Sleeves, Depuy Orthopaedics, Inc., 2010, 0612-92-509, 4 Pages.
European Search Report for Corresponding App. No. 13167346.9-1654 Dated Jul. 24, 2013, 5 Pages.

\* cited by examiner

PROSTHESIS KIT WITH FINNED SLEEVE

TECHNICAL FIELD

The present disclosure relates generally to prosthetic joints, and more particularly to a modular prosthetic joint system that includes a metaphyseal component.

BACKGROUND

The knee joint basically consists of the bone interface of the distal end of the femur and the proximal end of the tibia. Appearing to cover or at least partially protect this interface is the patella, which is a sesamoid bone within the tendon of the long muscle (quadriceps) on the front of the thigh. This tendon inserts into the tibial tuberosity and the posterior surface of the patella is smooth and glides over the femur.

The femur is configured with two knob like processes (the medial condyle and the lateral condyle) which are substantially smooth and which articulate with the medial plateau and the lateral plateau of the tibia, respectively. The plateaus of the tibia are substantially smooth and slightly cupped thereby providing a slight receptacle for receipt of the femoral condyles.

When the knee joint is damaged whether as a result of an accident or illness, a prosthetic replacement of the damaged joint may be necessary to relieve pain and to restore normal use to the joint. Typically the entire knee joint is replaced by means of a surgical procedure that involves removal of the surfaces of the corresponding damaged bones and replacement of these surfaces with prosthetic implants. This replacement of a native knee joint with a prosthetic joint is referred to as a primary total-knee arthroplasty.

On occasion, the primary knee prostheses fails. Failure can result from many causes, including wear, aseptic loosening, osteolysis, ligamentous instability, arthrofibrosis and patellofemoral complications. When the failure is debilitating, revision knee surgery may be necessary. In a revision, the primary knee prosthesis is removed and replaced with components of a revision prosthetic knee system.

Knee implant systems for both primary and revision applications are available from a variety of manufacturers, including DePuy Orthopaedics, Inc. of Warsaw, Ind. DePuy and others offer several different systems for both primary and revision applications. For example, DePuy Orthopaedics offers the P.F.C. SIGMA® Knee System, the LCS® Total Knee System, and the S-ROM Modular Total Knee System. Each of these orthopaedic knee systems includes several components, some appropriate for use in primary knee arthroplasty and some appropriate for use in revision surgery.

DePuy Orthopaedics also offers other orthopaedic implant systems for other applications. One such system is the LPS System. The LPS System is provided for use in cases of severe trauma and disease. In such cases, the trauma or disease can lead to significant amounts of bone loss. The LPS System provides components that can replace all or significant portions of a particular bone, such as the femur. The DePuy LPS System is described more fully in U.S. patent application Ser. No. 10/135,791, entitled "Modular Limb Preservation System", filed Apr. 30, 2002 by Hazebrouck et al., which is incorporated by reference herein in its entirety.

In some patients, the metaphysis of the bone near the joint presents cavitary defects that are not completely filled by standard knee implants. The presence of such metaphyseal defects can result in loosening of the prosthetic implant over time, compromising the stability of the prosthetic implant and frequently requiring revision of the prosthetic implant.

To fill metaphyseal cavitary defects, knee systems with modular metaphyseal sleeves have been provided. Such sleeves are illustrated, for example, in: U.S. Pat. Pub. No. 2010/0114323, entitled "Knee Prosthesis Kit with Winged Sleeves and Milling Guide;" U.S. Pat. Pub. No. 2006/0030945A1, entitled "Modular Orthopaedic Implant System With Multi-Use Stems;" U.S. Pat. No. 7,799,085, entitled "Modular Implant System With Fully Porous Coated Sleeve;" U.S. Pat. No. 7,291,174, entitled "Prosthetic Tibial Component With Modular Sleeve;" U.S. Pat. No. 6,171,342, entitled "Medical Fastening System;" U.S. Pat. No. 5,824,097, entitled "Medical Fastening System;" U.S. Pat. No. 5,782,921, entitled "Modular Knee Prosthesis;" and U.S. Pat. No. 4,634,444, entitled "Semi-Constrained Artificial Joint." Such sleeves have been used in commercially available prosthetic knee implant systems, such as the P.F.C. SIGMA.® Knee System, the LCS® Total Knee System, the S-ROM Modular Total Knee System and the LPS System, all available from DePuy Orthopaedics, Inc. of Warsaw, Ind.

Modular sleeves have also been used in hip implant systems, as illustrated, for example, in: U.S. Pat. No. 6,264,699, entitled "Modular Stem and Sleeve Prosthesis;" and U.S. Pat. No. 4,790,852, entitled "Sleeves for Affixing Artificial Joints to Bone." Such hip sleeves have been used in commercially available prosthetic hip implant systems, such as the S-ROM hip systems, available from DePuy Orthopaedics, Inc. of Warsaw, Ind.

The disclosures of all of the above patent applications and patents are incorporated by reference herein in their entireties.

In knee systems with modular metaphyseal sleeves, the conventional shape of many of the sleeves is generally an elliptical cone with a large ellipse profile close to the joint line tapering down to a smaller elliptical or circular profile at the termination of the component distal to the joint line. Generally, the sleeves have a terraced or stepped outer surface and an inner channel for frictional fixation to another component. This geometry fills cavitary defects in the metaphysis, allows for a wider surface area for load transfer through the joint and provides rotational stability for the articulating components of the prosthesis.

In some knee-arthroplasty patients, metaphyseal defects may be single sided: there may be a medial or lateral defect that requires use of a metaphyseal sleeve but the opposite side may have healthier bone. To use a conventional symmetric sleeve in such cases would require the sacrifice of some healthy bone that could have been left in place to provide support for the prosthesis. Some have attempted to address single-side defects through use of augments; however, such systems address only peripheral defects and do not account for situations where the peripheral bone is intact but there is a central void.

U.S. Pat. Pub. No. 2010/0114323, entitled "Knee Prosthesis Kit with Winged Sleeves and Milling Guide," referenced above, discloses an asymmetric metaphyseal sleeve that may be advantageously used in patients having single-side defects in the metaphysis. The metaphyseal sleeves illustrated in that patent application include two forms, one with a single protrusion (wing or spout) to extend in a generally medial or lateral direction in the case of a non-centralized defect in the tibia or femur and one with two protrusions (wings or spouts) to extend in both a generally medial or lateral direction in the case of a centralized defect in the tibia or femur.

In hip systems with modular metaphyseal sleeves, the conventional shape of many of the sleeves is generally a frusto-conical cone with a protrusion (wing or spout) extending radially outward. The spout or wing is intended to be placed on the medial side of the proximal hip metaphysis, opposite from the greater trochanter. Generally, such hip sleeves also have a terraced or stepped outer surface and an inner channel for frictional fixation to another component. This geometry fills cavitary defects in the medial metaphysis, allows for a wider surface area for load transfer through the joint and provides rotational stability for the articulating components of the prosthesis.

SUMMARY

The present invention provides a knee implant system with a new metaphyseal sleeve design for use in the case of a non-centralized defect in the tibia or femur, the new metaphyseal sleeve design providing increased stability with minimal sacrifice of bone tissue. The present invention also provides a hip implant system with stabilized metaphyseal sleeves.

According to one aspect of the present disclosure, a modular knee prosthesis kit is provided. The kit includes a femoral component, a tibial component and a sleeve. The femoral component has condylar surfaces and the tibial component has condylar surfaces to articulate with the condylar surfaces of the femoral component. The sleeve comprises first and second ends, a central portion, a terraced side wing, a fin, and an inner wall defining a channel extending from the first end to the second end. The channel has a central longitudinal axis and tapers from the first end toward the second end. The inner wall has edges defining a circular opening at the first end and a circular opening at the second end. The channel and circular openings are in the central portion of the sleeve. The terraced side wing includes a plurality of adjacent terraces, each terrace having an outer edge around its perimeter. The outer edge of each terrace lies in a plane substantially perpendicular to the central longitudinal axis of the channel. The fin includes a pair of outer surfaces extending outward from the central portion of the sleeve. The outer surfaces are spaced from each other a first distance nearest the first end of the sleeve and a second smaller distance nearest the second end of the sleeve to define a wedge-shape. The outer surfaces of the fin are continuous and non-terraced.

In an illustrative embodiment, the fin has a fin edge connecting the outer surfaces of the fin. The fin edge is spaced from the junctions of the outer surfaces of the fin and the central portion of the sleeve. In a more particular embodiment, the fin edge tapers toward the central longitudinal axis of the channel of the sleeve so that the smallest distance between the central longitudinal axis and the fin edge is nearest the second end of the sleeve and the greatest distance between the central longitudinal axis and the fin edge is nearest the first end of the sleeve. In another more particular embodiment, the outer surfaces of the fin taper toward the fin edge; the outer surfaces of the fin may taper toward the second end of the sleeve. In this embodiment, the fin edge may taper toward the central longitudinal axis of the channel of the sleeve so that the smallest distance between the central longitudinal axis and the fin edge is nearest the second end of the sleeve and the greatest distance between the central longitudinal axis and the fin edge is nearest the first end of the sleeve.

In another illustrative embodiment, the outer surfaces of the fin taper toward the second end of the sleeve. The outer surfaces of the fin may be concavely curved.

In another illustrative embodiment, the central portion of the sleeve has an outer surface that includes terraced and non-terraced portions.

In another illustrative embodiment, the tibial component comprises a tibial tray having a stem and a tibial insert carried by the tibial tray. In this embodiment, the sleeve defines a tibial sleeve, and the tibial sleeve and the stem are sized and shaped so that the tibial sleeve is mountable on the stem with the stem extending through the channel of the tibial sleeve and frictionally locked to the tibial sleeve.

In another illustrative embodiment, the kit further includes a femoral adapter mountable to the femoral component. In this embodiment, the sleeve defines a femoral sleeve, and the femoral sleeve and the femoral adapter are sized and shaped so that the femoral sleeve is mountable on the adapter with the adapter extending through the channel of the femoral sleeve and frictionally locked to the femoral sleeve.

According to another aspect of the present disclosure, a modular knee prosthesis kit is provided. The kit includes a femoral component, a tibial component and a sleeve. The femoral component has condylar surfaces and the tibial component has condylar surfaces to articulate with the condylar surfaces of the femoral component. The sleeve comprises first and second ends, a central portion, a terraced side wing, a fin, and an inner wall defining a channel extending from the first end to the second end. The channel has a central longitudinal axis and tapers from the first end toward the second end. The inner wall has edges defining a circular opening at the first end and a circular opening at the second end. The channel and circular openings are in the central portion of the sleeve. The terraced side wing includes a plurality of adjacent terraces. Each terrace has an outer edge around its perimeter, the outer edge of each terrace lying in a plane substantially perpendicular to the central longitudinal axis of the channel. The terraced side wing includes a first surface nearest the first end of the sleeve. The first surface has an outer edge including a curved end portion and wing segments positioned between the curved end portion and the central portion of the sleeve. The curved end portion defines a wing apex wherein the radial distance between the central longitudinal axis of the channel and the wing apex is the maximum radial distance between the central longitudinal axis of the channel and any portion of the outer edge of the surface of the terraced side wing. The fin includes a first surface nearest the first end of the sleeve. This first surface has an outer edge that includes a fin apex at the maximum radial distance between the central longitudinal axis of the channel and any portion of the outer edge of the fin. The outer edge of the fin includes two fin segments positioned between the fin apex and the central portion of the sleeve. The curved end portion of the outer edge of the terraced side wing is convex. Each fin segment is selected from the group consisting of a concavely curved fin segment and a straight fin segment lying along a line intersecting the fin apex.

In an illustrative embodiment, the outer surface of the fin is not terraced.

In another illustrative embodiment, the fin has a fin edge extending from the fin apex toward the second end of the body of the sleeve and the fin edge tapers toward the central longitudinal axis of the channel of the sleeve.

In another illustrative embodiment, the fin has a maximum thickness at the first end of the sleeve and a minimum thickness at the second end of the sleeve.

In another illustrative embodiment, the tibial component comprises a tibial tray having a stem and a tibial insert carried by the tibial tray. In this embodiment the sleeve defines a tibial sleeve. The tibial sleeve and the stem are sized and shaped so that the tibial sleeve is mountable on the stem with the stem extending through the channel of the tibial sleeve and the stem frictionally locked to the tibial sleeve.

In another illustrative embodiment, the kit further includes a femoral adapter mountable to the femoral component. In this embodiment the sleeve defines a femoral sleeve. The femoral sleeve and the femoral adapter are sized and shaped so that the femoral sleeve is mountable on the adapter with the adapter extending through the channel of the femoral sleeve and the adapter frictionally locked to the femoral sleeve.

In another illustrative embodiment, the central portion of the sleeve has an outer surface that includes terraced and non-terraced portions.

In another illustrative embodiment, the wing apex, fin apex and central longitudinal axis of the channel are co-planar.

In another illustrative embodiment, the wing apex and central longitudinal axis of the channel lie in one plane and the fin apex and central longitudinal axis of the channel lie in a separate plane.

In another illustrative embodiment, the kit also includes a sleeve with two terraced side wings.

In another illustrative embodiment, the outer edges of the first surfaces of the side wing and the fin are co-planar.

In another illustrative embodiment, the fin includes outer surfaces extending from the fin segments of the outer edge of the first surface of the fin toward the second end of the sleeve and the outer surfaces of the fin taper toward the second end of the sleeve. In a more particular embodiment, the outer surfaces of the fin are continuous and non-terraced. In another more particular embodiment, the fin has a fin edge extending from the fin apex toward the second end of the body of the sleeve. In this embodiment, the fin edge tapers toward the central longitudinal axis of the channel of the sleeve. In this embodiment, the outer surfaces of the fin may be continuous and non-terraced. In this embodiment, the central portion of the sleeve may have a surface at the first end of the sleeve, the surface having an outer edge with opposed curved portions. In this embodiment, the opposed curved portions of the outer edge of the central portion may be co-planar with the wing apex and fin apex.

According to another aspect of the present disclosure, a sleeve has first and second ends, a terraced portion, a fin and an inner wall defining a channel between the first and second ends. The sleeve has an axial length between the first and second ends and the channel has a central longitudinal axis. The terraced portion includes a plurality of adjacent terraces. Each terrace has an outer edge around its perimeter. The outer edge of each terrace lies in a plane substantially perpendicular to the central longitudinal axis of the channel. The fin includes a pair of outer surfaces spaced from each other at a first distance nearest the first end of the sleeve and a second smaller distance nearest the second end of the sleeve to define a wedge shape. The outer surfaces of the fin are continuous and non-terraced.

In an illustrative embodiment, the terraced portion includes a central frusto-conical portion surrounding the channel. In this embodiment the fin extends radially outwardly from the central frusto-conical portion. In a more particular embodiment, the terraced portion includes a wing portion extending radially outwardly from the central frusto-conical portion in a direction different from the fin.

In another illustrative embodiment, the fin has an axial length less than the axial length of the sleeve.

In another illustrative embodiment, the fin has a fin edge connecting the outer surfaces of the fin; the fin edge is spaced from the terraced portion of the sleeve. In a more particular embodiment, the fin edge tapers toward the central longitudinal axis of the channel so that the smallest distance between the central longitudinal axis and the fin edge is nearest the second end of the sleeve and the greatest distance between the central longitudinal axis and the fin edge is nearest the first end of the sleeve. In this embodiment, the outer surfaces of the fin may taper toward the fin edge and toward the second end of the sleeve. In this embodiment, the outer surfaces of the fin may be concavely curved.

In another illustrative embodiment, the sleeve is part of a hip prosthesis system including a stem extending out from the second end of the sleeve, a neck extending out from the first end of the sleeve and an articulating ball extending out from the neck.

In an illustrative embodiment, the sleeve is part of a knee prosthesis system including a femoral component with condylar surfaces, a tibial component with condylar surfaces to articulate with the condylar surfaces of the femoral component and a stem extension, and wherein the sleeve is connected to the stem extension and to one of the femoral component and the tibial component connected by complementary locking tapers.

BRIEF DESCRIPTION OF THE DRAWINGS

The detailed description particularly refers to the accompanying figures in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the disclosure to the particular forms disclosed, but on the contrary, the intention is to cover all modifications, equivalents, and alternatives following within the spirit and scope of the invention as defined by the appended claims.

Terms representing anatomical references, such as anterior and posterior, medial and lateral, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Figure 1:
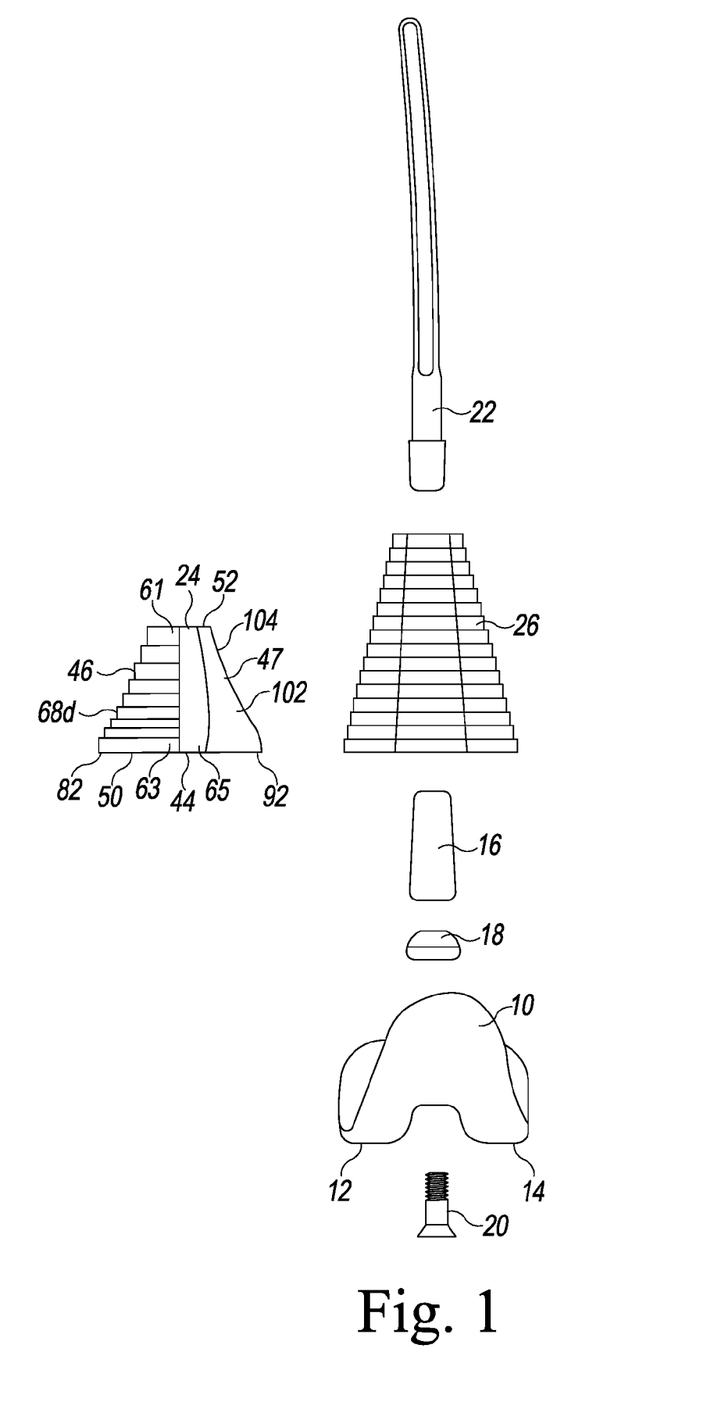
FIG. 1 is a view of the femoral components of a modular knee prosthesis kit.
Figure 2:
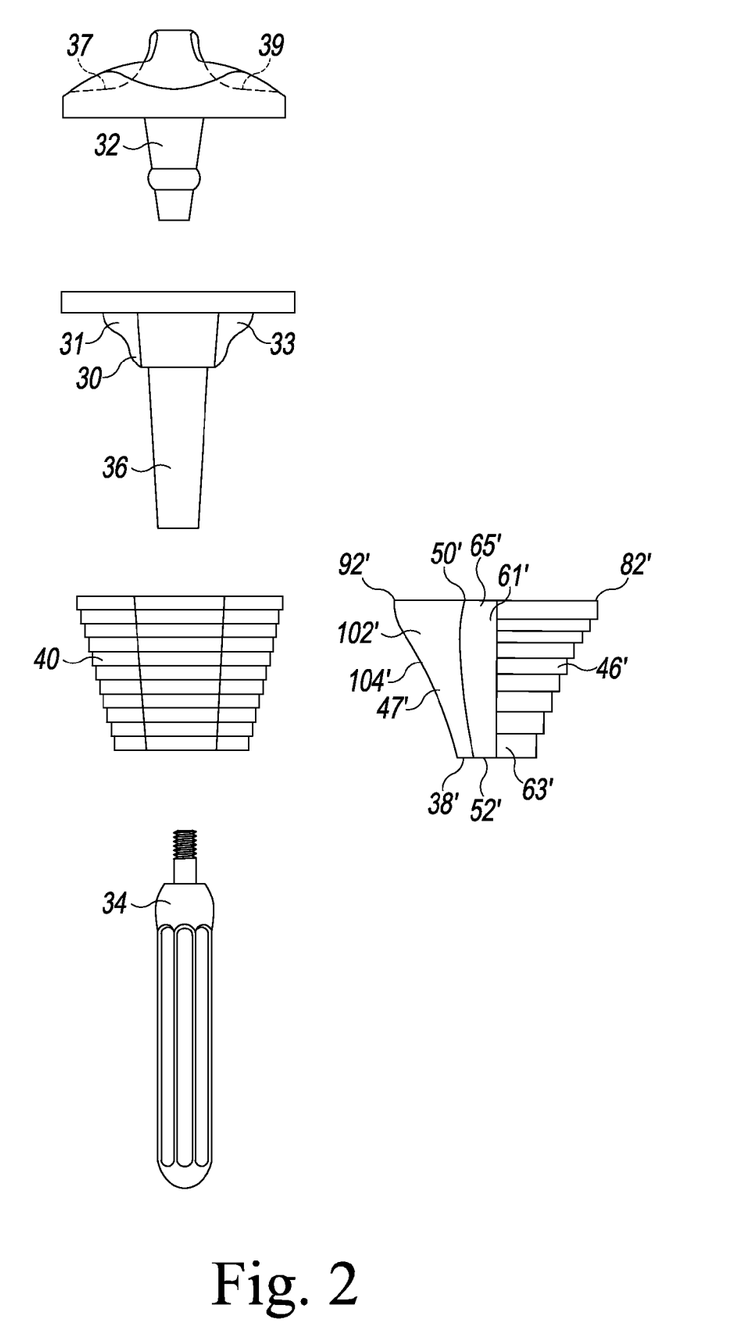
FIG. 2 is a view of the tibial components of a modular knee prosthesis kit.

FIGS. 1 and 2 illustrate an example of components of a modular knee prosthesis kit. As illustrated in FIG. 1, on the femoral side, the kit includes a distal femoral component 10 with curved convex condylar surfaces 12, 14. The illustrated distal femoral component is a posterior stabilized component. A femoral adapter 16 is also provided, along with a collar 18 for placement between the adapter 16 and the distal femoral component 10. A bolt 20 is provided for connecting the adapter 16, collar 18 and distal femoral component 10 together. The adapter 16 has an outer surface that is smooth and tapered. A stem extension 22 is also provided. All of the above components may be standard parts of the P.F.C. SIGMA.® Knee System available from DePuy Orthopaedics, Inc. of Warsaw, Ind. The adapter may have features such as those illustrated in U.S. Pat. Pub. No. 2006/0030945, entitled "Modular Orthopaedic Implant System with Multi-Use Stems," or those illustrated in U.S. Pat. No. 6,171,342, entitled "Medical Fastening System," U.S. Pat. No. 5,824,097, entitled "Medical Fastening System," U.S. Pat. No. 5,782,921, entitled "Modular Knee Prosthesis." Also as described in U.S. Pat. Pub. No. 2006/0030945, the stem extension may have features other than those illustrated in FIG. 1. It should be understood that these components are described for purposes of illustration only; the present invention is not limited to any particular type of distal femoral component or stem or any other particular component unless expressly called out in the claims.

As illustrated in FIG. 1, the femoral components of the kit also include two types of metaphyseal sleeves 24, 26. As described in more detail below, one of the metaphyseal sleeves 24 is a single-wing (or single-spout) sleeve provided for use in a single-side defect in the metaphysis of the bone and the other metaphyseal sleeve 26 is a double-wing (or double-spout) sleeve provided for use where both sides of the metaphysis are to be filled.

As illustrated in FIG. 2, on the tibial side, the kit includes a tibial tray component 30, a tibial bearing insert 32 and a stem extension 34. The illustrated tibial tray component 30 is a commercial MBT Revision tibial tray, available from DePuy Orthopaedics, Inc. of Warsaw, Ind. The tray component 30 has an integral stem portion 36 with a bore (not shown) with internal threads to which the stem extension 34 may be attached. The outer surface of the stem portion 36 has a smooth finish, tapers away from the joint motion surface and is connected to the inferior surface of the tibial tray component 30 through keels 31, 33. The joint motion surface corresponds with the juncture of the curved convex condyles 12, 14 of the distal femoral component 10 and the curved concave condylar surfaces of the tibial bearing insert 32 (the curved concave condylar surfaces of the tibial bearing insert being shown in FIG. 2 in phantom at 37, 39). The distal femoral component and the tibial component articulate along the joint motion surface as the knee flexes and extends. It should be understood that these tibial components are described for purposes of illustration only; the present invention is not limited to any particular type of tibial component or stem or any other particular component unless expressly called out in the claims.

As illustrated in FIG. 2, the tibial components of the kit also include two types of metaphyseal sleeves 38, 40. As described in more detail below, one of the metaphyseal sleeves 38 is a single-wing sleeve provided for use in a single-side defect in the metaphysis of the bone and the other metaphyseal sleeve 40 is a double-wing sleeve provided for use where both sides of the metaphysis are to be filled.

A first example of a prosthetic single-wing metaphyseal sleeve implant 24 is illustrated in FIGS. 3-7. Unless otherwise noted, it should be understood that the following description also applies to the single-wing metaphyseal sleeve 38 for use with the tibial component.

Figure 4:
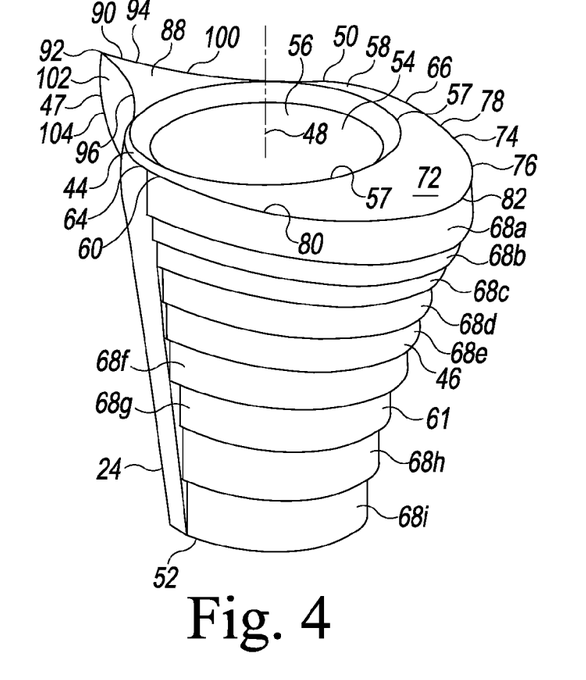
FIG. 4 is a perspective View of the single-wing metaphyseal sleeve component of FIG. 3.
Figure 5:
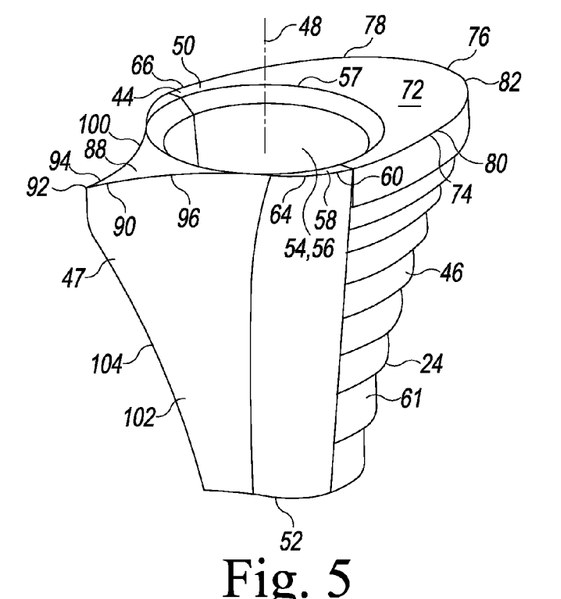
FIG. 5 is another perspective view of the single-wing metaphyseal sleeve component of FIGS. 3-4.
Figure 6:
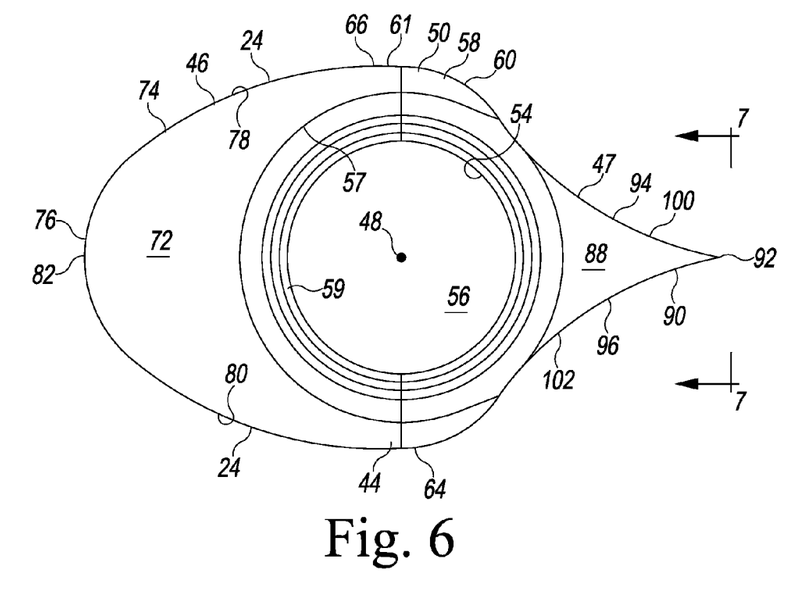
FIG. 6 is a top plan view of the single-wing metaphyseal sleeve component of FIGS. 3-5.
Figure 7:
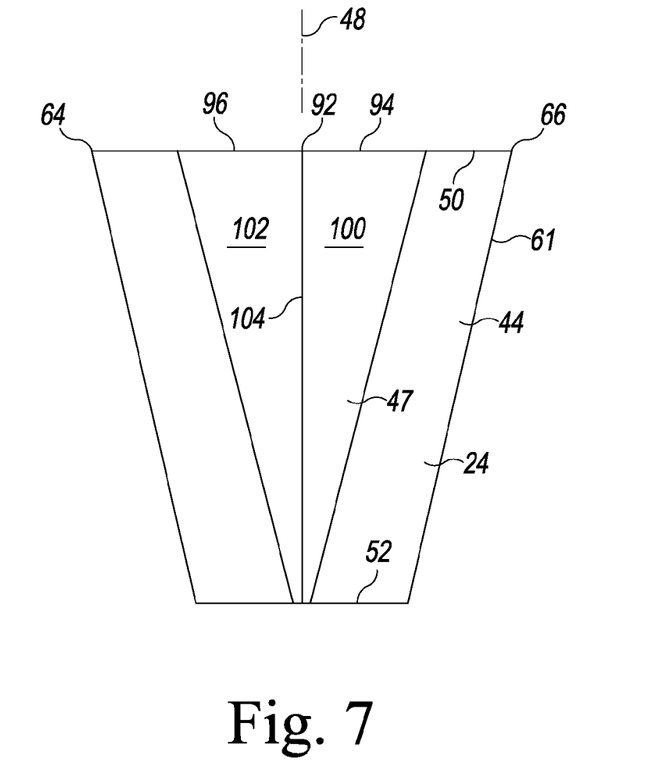
FIG. 7 is an end view of the single-wing metaphyseal sleeve component of FIGS. 3-6, taken along line 7-7 of FIG. 6.

The first illustrated single-wing sleeve 24 is designed for use in a bone wherein the condition of the bone requires additional support or fixation on either the medial or lateral side of the metaphysis of the bone, but not on both sides; such a defect in the bone may be characterized as a non-centralized defect. The illustrated single-wing sleeve 24 comprises a central portion 44, a terraced side wing portion 46 and a fin 47. As shown in FIGS. 4-6, the central portion 44 has an inner wall 54 defining a channel 56 having a central longitudinal axis 48. The single-wing sleeve 24 has a first end 50 and a second end 52. The first end 50 is the wider end, and is intended to face toward the joint motion surface. The second end is the more narrow end, and is intended to face away from the joint motion surface.

The tapered channel 56 tapers from the first end 50 toward the second end 52 and may have any suitable taper angle for frictional locking with another element; for example, the tapered channel 56 may define a Morse taper. Accordingly, the inner wall 54 has an edge 57 at the first end 50 defining a circular opening and an edge 59 at the second end 52 (shown in FIG. 6) defining a smaller diameter circular opening. The channel 56 is in the central portion 44 of the sleeve 24 and is designed to receive the tapered surface of the adapter 16 on the femoral side or the tapered surface of the stem portion 36 of the tibial tray 30 and to frictionally lock with one of these elements. Although it may be desirable to provide a set of sleeves 24 that can be used on either the tibial or the femoral side, it should be understood that it is also within the scope of the present invention to provide sleeves 24 that are designed to be used on the femoral side and a separate set of sleeves that are designed to be used on the tibial side; the shape of the channels 56 in such elements may vary to frictionally engage the adapter 16 if the sleeve is a femoral metaphyseal sleeve or to frictionally engage the stem portion 36 of the tibial tray 30. The channel may have a different taper at the second end 52 to frictionally lock or engage with a complementary tapered post, such as the post shown at the end of the stem 22 in FIG. 1.

As shown in FIGS. 3-7, the central portion 44 of the sleeve 24 in the illustrated embodiment has a surface 58 at the first end 50 of the sleeve with an outer edge 60 around at least part of its perimeter and around the edge 57 defining the circular opening into the channel 56. This outer edge 60 includes two diametrically-opposed curved portions 64, 66.

The central portion 44 of the sleeve 24 also has an outer surface 61. In the embodiment of FIGS. 1-7, the outer surface 61 of the central portion 44 includes a terraced portion 63 and a non-terraced portion 65 (see FIG. 3). In this embodiment, the terraced portion 63 of the outer surface 61 extends from a central plane to the terraced side wing 46 and the non-terraced portion 65 extends from the central plane to the fin 47.

Figure 3:
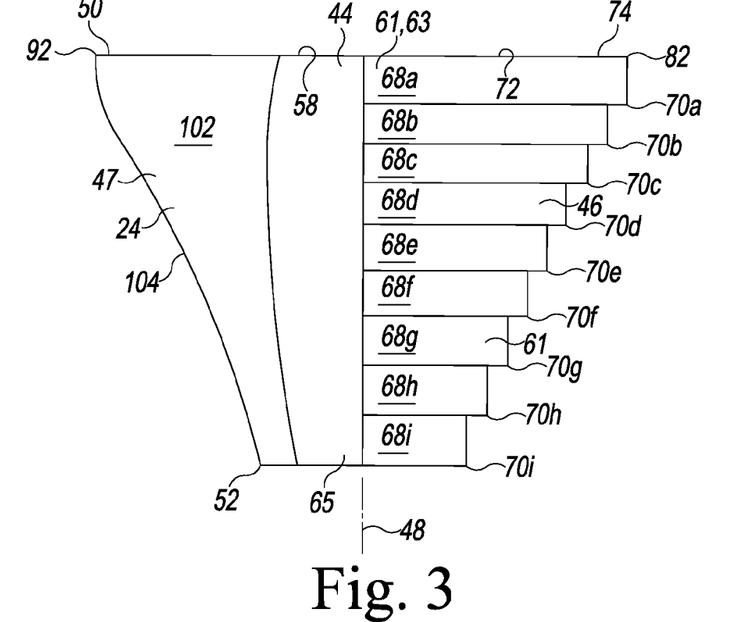
FIG. 3 is a front view of the single-wing metaphyseal sleeve component of the kit of FIGS. 1-2.

The terraced side wing 46 includes a plurality of adjacent terraces or steps. In the first illustrated embodiment, the terraced side wing 46 has nine adjacent terraces or steps, designated 68a-68i in FIGS. 3-4. As shown in FIG. 3, each terrace 68a-68i has an outer edge 70a-70i around its perimeter. As shown in FIG. 3, the outer edges 70a-70i of the terraces 68a-68i lie in planes that are substantially perpendicular to the central longitudinal axis 48 of the channel.

The terraced side wing 46 also has an exposed first surface 72 at the terrace 68a nearest the first end 50 of the sleeve 24. This surface has an outer edge 74 including a curved end portion 76 and wing segments 78, 80 (see FIGS. 4-6). The wing segments 78, 80 are positioned between the curved end portion 76 and the central portion 44 of the sleeve 24. The curved end portion 76 is a convex curve and defines a wing apex 82; the radial distance between the central longitudinal axis 48 of the channel 56 and the wing apex 82 is the maximum radial distance between the central longitudinal axis 48 and any portion of the outer edge 74 of the first surface 72 of the terraced side wing 46.

The fin 47 includes a first surface 88 nearest the first end 50 of the single-wing metaphyseal sleeve 24. In the illustrated embodiment, the first surface 88 lies in a plane that is substantially perpendicular to the central longitudinal axis 48 of the channel 56. The first surface of the fin 47 has an outer edge 90 that includes a fin apex portion 92 and two fin segments 94, 96. The fin apex 92 is at the maximum radial distance between the central longitudinal axis 48 of the channel 56 and any portion of the outer edge 90. The two fin segments 94, 96 are positioned between the fin apex 92 and the central portion 44 of the sleeve.

In the first illustrated embodiment, the two fin segments 94, 96 comprise concave curves meeting at the fin apex 92. As discussed below, the two fin segments 94, 96 may alternatively comprise straight lines meeting at the fin apex portion 92A (see FIG. 8). Alternatively, the two fin segments could comprise a straight fin segment and a concavely curved segment.

It should be understood that although FIGS. 4-6 show the fin apex 92 as a point, the apex 92 may comprise a small radius or small segment. Essentially, the fin 47 operates as a wedge as the sleeve is implanted, and is intended to cut through the bone as the sleeve is pushed into the bone. The fin 47 is preferably sized and shaped to optimize this wedging function and to stabilize the sleeve against torsion but with minimal sacrifice of bone tissue. Optimally, the maximum distance between the fin segments 94, 96 is minimized but is great enough to provide adequate strength to the connection between the fin 47 and the remainder of the sleeve.

The fin 47 also includes outer surfaces 100, 102 that extend outward from the central portion 44 of the sleeve 24, and from the two fin segments 94, 96 and fin apex 92 nearest the first end 50 of the sleeve 24 toward the second end 52 of the sleeve 24. These outer surfaces 100, 102 are spaced from each other a first distance nearest the first end 50 of the sleeve 24 and a second smaller distance nearest the second end 52 of the sleeve to define a wedge-shape. Thus, the outer surfaces 100, 102 taper toward each other in an axial direction toward the second end 52 of the sleeve.

The outer surfaces 100, 102 of the fin 47 also taper toward each other in a radial direction, connecting to each other along an outer fin edge 104. Along multiple planes perpendicular to the central longitudinal axis 48 of the channel 56, the outer fin edge 104 defines the maximum radial dimension of the fin from the central longitudinal axis 48. This outer fin edge 104 tapers toward the central longitudinal axis 48 so that the smallest distance between the outer fin edge 104 and the central longitudinal axis 48 is nearest the second end 52 of the sleeve 24 and the greatest distance between the central longitudinal axis 48 and the outer fin edge 104 is nearest the first end 50 of the sleeve 24. The outer fin edge 104 may comprise a line, although a small radius or small segment may be used to connect the two outer surfaces 100, 102 along the edge 104.

The outer surfaces 100, 102 of the fin 47 are continuous and non-terraced. In the first illustrated embodiment, these outer surfaces 100, 102 are concavely curved in two directions. It should be understood that other shapes, such as flat converging surfaces (see FIG. 8), could be used for the fin outer surfaces.

The sleeve 24 may have additional features, such as porous coating, for example, to enhance fixation. For example, the sleeve 24 could have a porous coating as disclosed in U.S. Pat. No. 7,799,085, entitled "Modular Implant System With Fully Porous Coated Sleeve." Such a porous coating could be applied to: all or part of the terraced side wing 46; all or part of the central portion 44; and all or part of the fin 47. Alternatively, some of the sleeve 24 could be left without any porous coating; for example, the fin 47 could be left smooth and without any porous coating. It should be understood that the sleeves could also use less porous coating than described in U.S. Pat. No. 7,799,085. All of the implant components of the kit may be made of standard materials used for prosthetic knee systems, such as standard titanium and cobalt-chromium alloys for the metal parts and standard polyethylenes for bearings, for example.

If the single-wing metaphyseal sleeve is to be used as a tibial sleeve, such as that illustrated at 38 in FIG. 2, the sleeve may include features to accommodate the keels 31, 33 such as those disclosed in U.S. Pat. No. 7,291,174 entitled "Prosthetic Tibial Component with Modular Sleeve." Other features may be used with either the femoral or tibial single-wing sleeve.

In FIG. 2, parts analogous to those shown in FIG. 1 for the single-wing femoral sleeve 24 are numbered with the same reference numbers as used in FIG. 1, followed by the prime "'" symbol.

As illustrated in FIGS. 1 and 2, the modular knee implant system may also include traditional metaphyseal sleeves, such as a double-wing metaphyseal sleeve 26, 40. The double-wing metaphyseal sleeves 26, 40 may have features such as those disclosed in U.S. Pat. Pub. No. 2010/0114323A1, entitled "Knee Prosthesis Kit with Winged Sleeves and Milling Guide;" U.S. Pat. No. 7,799,085, entitled "Modular Implant System with Fully Porous Coated Sleeve;" U.S. Pat. No. 7,291,174, entitled "Prosthetic Tibial Component with Modular Sleeve;" U.S. Pat. No. 6,171,342, entitled "Medical Fastening System;" U.S. Pat. No. 5,824,097, entitled "Medical Fastening System;" U.S. Pat. No. 5,782,921, entitled "Modular Knee Prosthesis;" and U.S. Pat. No. 4,634,444, entitled "Semi-Constrained Artificial Joint." In addition, the double-wing metaphyseal sleeves 26, 40 may have features used in commercially available prosthetic knee implant systems, such as the P.F.C. SIGMA.® Knee System, the LCS® Total Knee System, the S-ROM Modular Total Knee System and the LPS System, all available from DePuy Orthopaedics, Inc. of Warsaw, Ind.

The modular knee implant system may also include instruments for preparing the bone to receive the implant components and instruments for implanting the implant components in the prepared bone surface. One example of a suitable set of instruments and suitable surgical procedure for use in preparing the bone to receive any of the metaphyseal sleeves 24, 26, 38, 40 is disclosed in U.S. Pat. Pub. No. 2010/0114323A1. As there disclosed, a milling guide could be used to prepare a cavity in the metaphyseal bone to receive either a single-wing sleeve or a double-wing sleeve. For a single-wing sleeve, a milling guide could be used to prepare the metaphyseal bone to receive the central portion and terraced side wing, such as those illustrated at 44 and 46; no special preparation step should be required to prepare the bone to receive the fin portion of the metaphyseal sleeve. Instead, the sleeve may be impacted into the cavity, with the wedge shape of the fin serving to clear a suitable path for the fin as the sleeve is driven in the bone. In any event, the kit of the present invention will allow the surgeon to intraoperatively select the most appropriate sleeve for the patient, thereby allowing for bone conservation if the condition of the bone allows.

Figure 8:
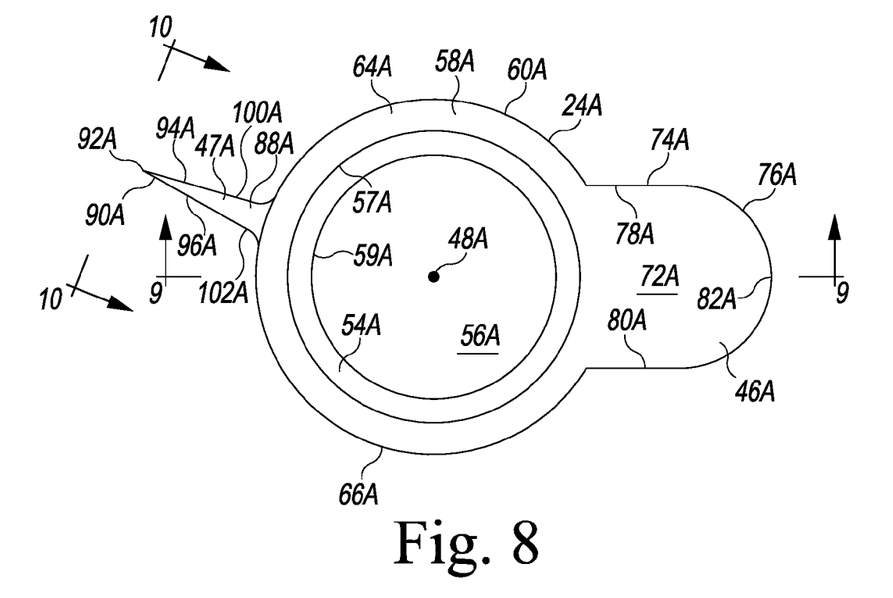
FIG. 8 is a top plan view of an alternative embodiment of a single-wing metaphyseal sleeve component that may be used in a modular knee prosthesis kit.
Figure 9:
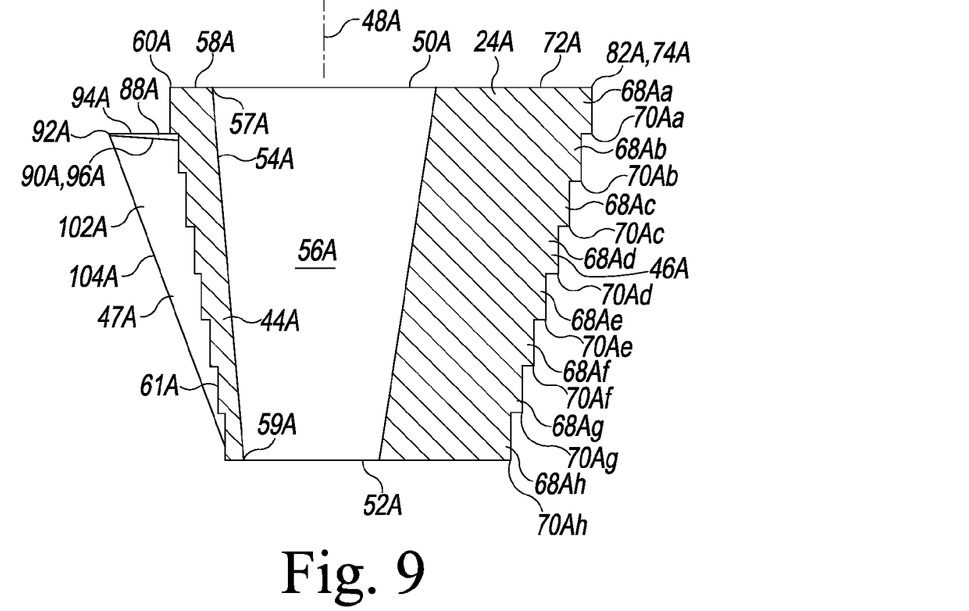
FIG. 9 is a cross-section of the single-wing metaphyseal sleeve component of the kit of FIG. 8, taken along line 9-9 of FIG. 8.
Figure 10:
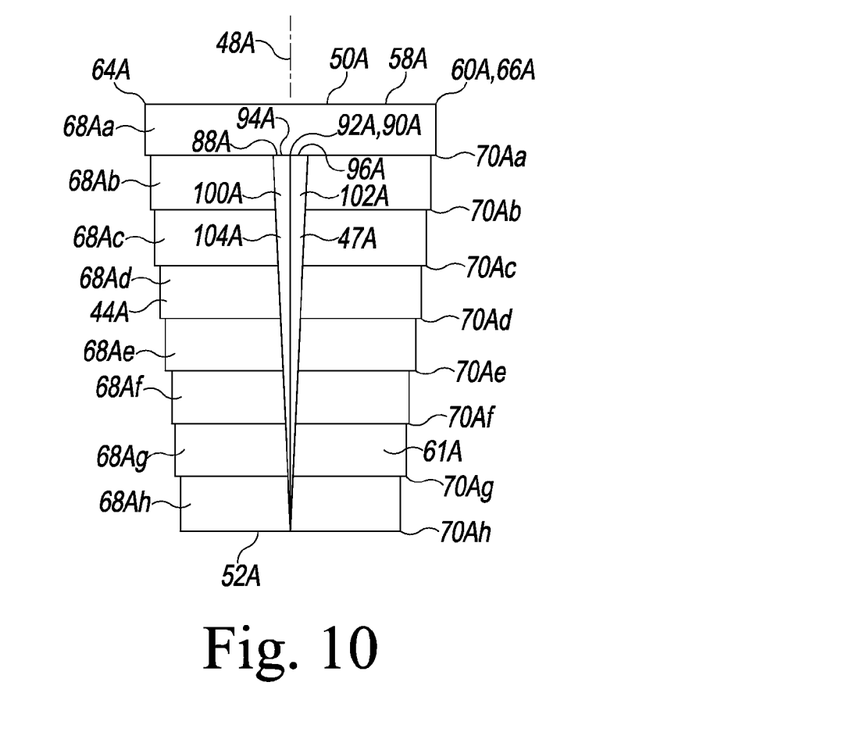
FIG. 10 is an end view of the single-wing metaphyseal sleeve component of FIGS. 8-9, taken along line 10-10 of FIG. 8.

An alternative embodiment of a single-wing metaphyseal sleeve component that may be used in a modular knee prosthesis kit is illustrated in FIGS. 8-10. Portions and parts of the single-wing metaphyseal sleeve component that are similar to portions or parts described above are identified with the same reference number, followed by the letter "A". The embodiment of FIGS. 8-10 differs from the embodiment of FIGS. 3-7 in several ways. First, while the wing apex 82, central longitudinal axis 48 and fin apex 92 in the embodiment of FIGS. 3-6 are aligned to be co-planar, in the embodiment of FIGS. 8-9, the wing apex 82A and central longitudinal axis 48A lie in one plane and the fin apex 92A and central longitudinal axis 48A lie in a separate plane that defines an obtuse angle with the plane of the wing apex 82A and central longitudinal axis 48A. Second, while the first surface 72 of the terraced side wing 46, surface 58 of the central portion 44 and first surface 88 of the fin 47 are co-planar in the embodiment of FIGS. 3-6, the first surface 88A of the fin 47A lies in a plane spaced from the plane of the first surface 72A and surface 58A of the terraced side wing 46A and central portion 44A in the embodiment of FIGS. 8-10. Third, while the fin segments 94, 96 of the embodiment of FIGS. 3-6 comprise concave curves, the fin segments 94A, 96A of the embodiment of FIGS. 8-9 comprise straight lines. Fourth, while the fin surfaces 100, 102 comprise concavely curved surfaces in the embodiment of FIGS. 3-6, the fin surfaces 100A, 102A of the embodiment of FIGS. 8-10 comprise flat, planar surfaces. Fifth, while only a portion of the outer surface 61 of the central portion 44 of the sleeve of FIGS. 3-6 is terraced, substantially all of the outer surface 61A of the central portion 44A of the sleeve of FIGS. 8-10 is terraced. Sixth, while the outer fin edge 104 of the embodiment of FIGS. 3-6 extends to the plane of the second end 52 of the sleeve and remains spaced from the central portion 44 at this end, in the embodiment of FIGS. 8-10 the outer fin edge 104A joins the central portion 44A of the sleeve at a position spaced from and between the first and second ends 50A, 52A of the sleeve. In addition, the side wing 47A in the embodiment of FIGS. 8-10 is shaped more similarly to the side wings described in U.S. Pat. Pub. No. 2010/0114323 than to the shape of the side wing 47 of the embodiment of FIGS. 3-6.

Figure 11:
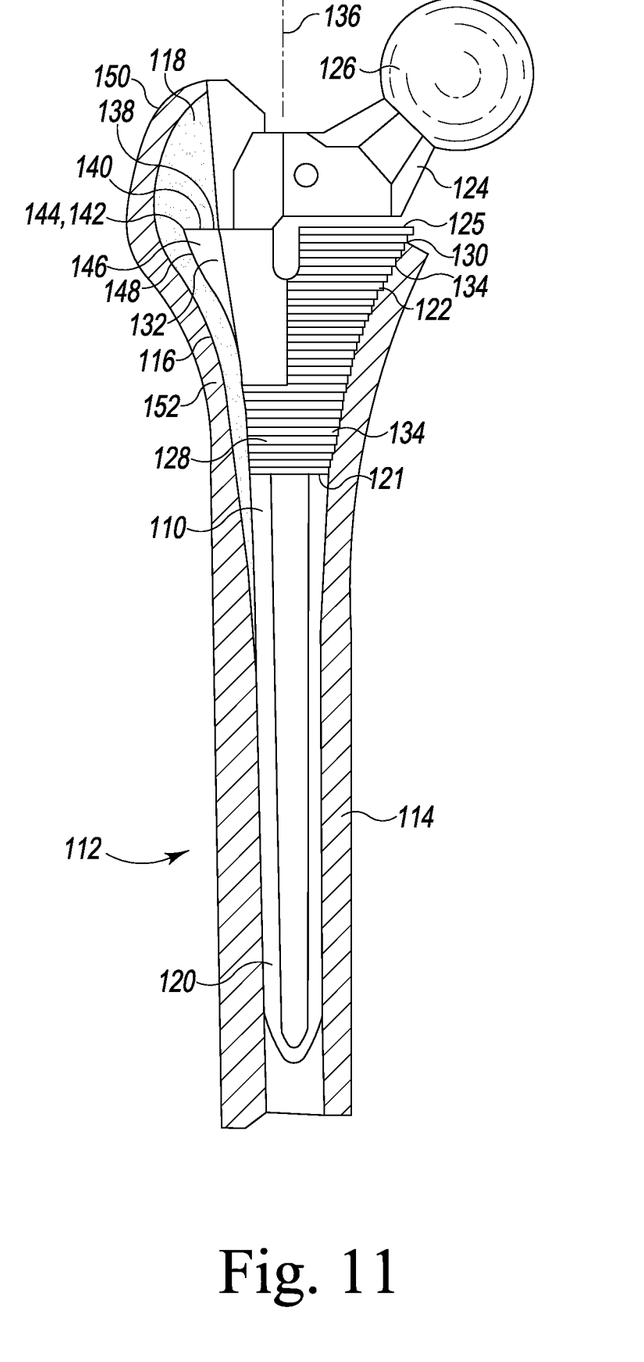
FIG. 11 is a cross-section of an example of the femoral components of a modular hip prosthesis, shown with a single-wing metaphyseal sleeve component.

FIG. 11 illustrates the principles of the present invention applied to the femoral components of a modular hip prosthesis system. As there shown, femoral component 110 of hip prosthesis 112 is implanted in the patient's femur 114, which has an outer shell 116 of hard cortical bone and an inner metaphysis 118 of softer bone. The femoral component 110 includes a stem 120 extending out from a second end 121 of a metaphyseal sleeve 122, neck portion 124 extending out from a first end 125 of the sleeve 122 and a ball 126 extending out from the neck portion 124 to articulate with the acetabular components (not shown) of the hip prosthesis system. The stem 120, sleeve 122, neck portion 124 and ball are all connected by complementary locking tapers.

The hip metaphyseal sleeve 122 of FIG. 11 includes a central frusto-conical portion 128, a medial wing or spout 130 and a stabilizing fin 132. In this embodiment, a part of the central frusto-conical portion 128 and all of the medial wing or spout 130 include a plurality of terraces 134. All of the terraces 134 have edges that lie in planes perpendicular to the central longitudinal axis 136 of the channel (not shown) in the hip metaphyseal sleeve 122. The wing or spout 130 and adjacent part of the central frusto-conical portion 128 may have characteristics of standard commercial hip metaphyseal sleeves as those disclosed in U.S. Pat. No. 4,790,852, for example.

The fin 132 of the hip metaphyseal sleeve 122 may be substantially similar to the fin 47 described above. Accordingly, the fin 132 has an end surface 138 that lies in a plane that is substantially perpendicular to the central longitudinal axis 136. The end surface 138 of the fin 132 has an outer edge 140 that includes a fin apex portion 142 and two fin segments (one segment shown in FIG. 11 at 144). The fin apex 142 is at the maximum radial distance between the central longitudinal axis 136 of the channel and any portion of the outer edge 140. The two fin segments are positioned between the fin apex 142 and the central portion 128 of the sleeve.

The two fin segments may comprise concave curves meeting at the fin apex 142 or may alternatively comprise straight lines meeting at the fin apex portion 142. Alternatively, the two fin segments could comprise a straight fin segment and a concavely curved segment.

As in the first embodiment, the fin 132 operates as a wedge as the sleeve is implanted, and is intended to cut through the bone as the sleeve is pushed into the bone. The fin 132 is preferably sized and shaped to optimize this wedging function and to stabilize the sleeve against torsion but with minimal sacrifice of bone tissue. Optimally, the maximum distance between the fin segments is minimized but is great enough to provide adequate strength to the connection between the fin 132 and the remainder of the sleeve.

The fin 132 also includes outer surfaces that extend outward from the central portion 128 of the sleeve 122, and from the two fin segments (including segment 144) and fin apex 142. One of these outer surfaces is shown in FIG. 11 at 146. These outer surfaces taper toward each other in both radial and axial directions and are connected to each other along an outer fin edge 148. This outer fin edge 148 tapers toward the central longitudinal axis 136. The outer fin edge 148 may comprise a line, although a small radius or small segment may be used to connect the two outer surfaces (surface 146 and the opposite surface, not shown) along the edge 104.

The outer surfaces of the fin 132 are continuous and non-terraced. In the embodiment of FIG. 11, these outer surfaces (including surface 146) are concavely curved in two directions. It should be understood that other shapes, such as flat converging surfaces could be used for the fin outer surfaces.

As shown in FIG. 11, the fin 132 of the illustrated hip sleeve 122 is sized and oriented so that when implanted, the fin 132 is received in the proximal femoral metaphysis near the greater trochanter (shown at 150 in FIG. 11). While the frusto-conical central portion 128 of the sleeve 122 extends into the subtrochanteric region 152, the axial length of the illustrated fin 132 is substantially less than the overall axial length of the hip sleeve 122 (between ends 121, 125) so that the fin 132 does not extend into the subtrochanteric region in the embodiment of FIG. 11.

To implant a hip prosthesis including the sleeve 122, the proximal femur may be prepared in the standard manner and the assembly implanted in the prepared bone with the fin 132 being wedged into the cancellous bone 118 of the metaphysis.

Figure 12:
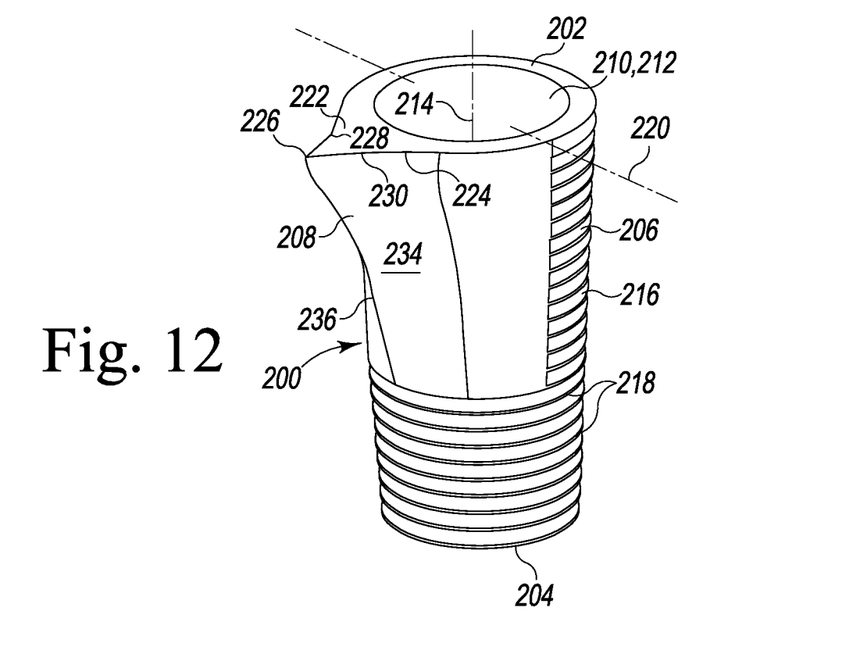
FIG. 12 is a perspective view of a metaphyseal sleeve component that may be provided as part of a modular hip prosthesis system or kit.
Figure 13:
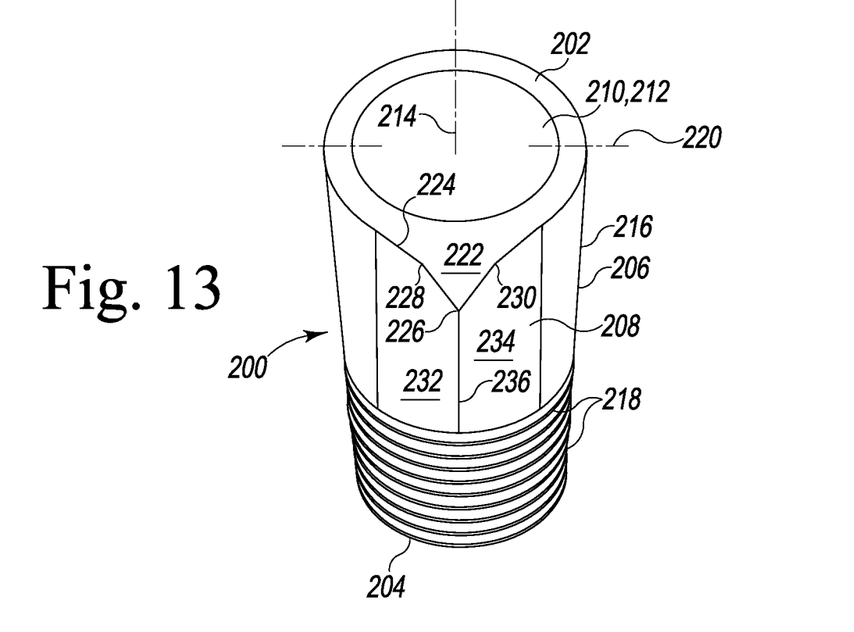
FIG. 13 is a perspective view of the metaphyseal sleeve component of FIG. 12.
Figure 14:
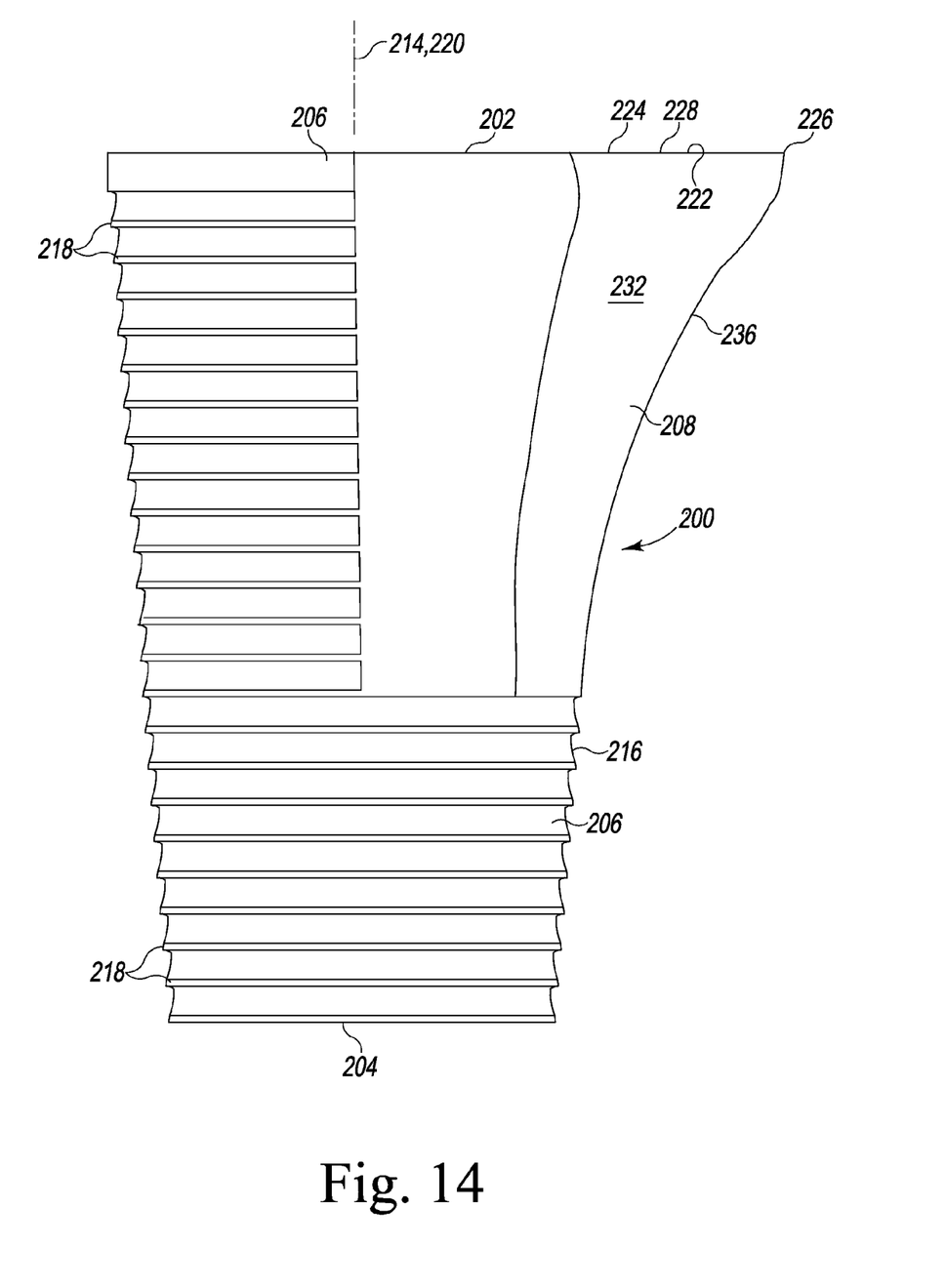
FIG. 14 is a side view of the metaphyseal sleeve component of FIGS. 12-13.

Another alternative sleeve design in illustrated in FIGS. 12-14. The sleeve 200 of this embodiment has a first end 202 that faces the joint motion surface when implanted, a second end 204 facing the bone diaphysis when implanted; the overall axial length of the sleeve 200 is between the two ends 202, 204. The sleeve 200 also has a central frusto-conical portion 206 and a fin 208. An inner wall 210 defines a channel 212 extending to circular openings in the first and second ends 202, 204. The channel has a central longitudinal axis 214. The fin 208 extends radially outward from the outer surface 216 of the central frusto-conical portion 206.

The sleeve 200 of the embodiment of FIGS. 12-14 is substantially the same as the sleeve 122 of FIG. 11 except that the sleeve 200 does not have a spout or wing like the spout or wing 130. Instead, the sleeve 200 of FIGS. 12-14 consists of the central frusto-conical portion 206 and fin 208.

In the embodiment of FIGS. 12-14, a part of the central frusto-conical portion 206 includes a plurality of terraces 218. All of the terraces 218 have edges that lie in planes perpendicular to the central longitudinal axis 214 of the channel. In this embodiment, the entire outer surface of the central portion 206 adjacent to the second end 204 includes terraces 218 and the entire outer surface of the central portion on one side of a plane 220 that includes the central longitudinal axis 214 includes terraces. The terraces may have characteristics like those described above, tapering from the first end 202 toward the second end 204.

The fin 208 of the sleeve 200 may be substantially similar to the fins 47, 132 described above. Accordingly, the fin 208 has an end surface 222 that lies in a plane that is substantially perpendicular to the central longitudinal axis 214. The end surface 222 of the fin 208 has an outer edge 224 that includes a fin apex portion 226 and two fin segments 228, 230. The fin apex 226 is at the maximum radial distance between the central longitudinal axis 214 of the channel and any portion of the outer edge 224. The two fin segments 228, 230 are positioned between the fin apex 226 and the central portion 206 of the sleeve 200.

The two fin segments 228, 230 may comprise concave curves meeting at the fin apex 226 or may alternatively comprise straight lines meeting at the fin apex portion 226. Alternatively, the two fin segments 228, 230 could comprise a straight fin segment and a concavely curved segment.

As in the first and second embodiments, the fin 208 operates as a wedge as the sleeve 200 is implanted, and is intended to cut through the bone as the sleeve is pushed into the bone. The fin 208 is preferably sized and shaped to optimize this wedging function and to stabilize the sleeve against torsion but with minimal sacrifice of bone tissue. Optimally, the maximum distance between the fin segments 228, 230 is minimized but is great enough to provide adequate strength to the connection between the fin 208 and the central portion 206 of the sleeve 200.

The fin 208 also includes outer surfaces 232, 234 that extend outward from the central portion 206 of the sleeve 200, and from the two fin segments 228, 230 and fin apex 226. These outer surfaces 232, 234 taper toward each other in both radial and axial directions and are connected to each other along an outer fin edge 236. This outer fin edge 236 tapers toward the central longitudinal axis 214. The outer fin edge 236 may comprise a line, although a small radius or small segment may be used to connect the two outer surfaces 232, 234 along the edge 236.

The outer surfaces 232, 234 of the fin 208 are continuous and non-terraced. These outer surfaces 232, 234 of the fin in the illustrated embodiment are concavely curved in two directions. It should be understood that other shapes, such as flat converging surfaces could be used for the fin outer surfaces 232, 234. The axial length of the illustrated fin 208 is substantially less than the overall axial length of the sleeve 200.

The sleeve 200 of the embodiment of FIGS. 12-14 could be used, for example, in either hip or knee arthroplasty in the manners described above for the other embodiments.

The differences between the above-described embodiments illustrate that variations may be made in kits embodying the principles of the present invention. The disclosed embodiments also illustrate that the principles of the present invention may be applied to joint prosthesis systems used to replace various joints of the body; it should be understood that the principles of the present invention may be applied to other joint prosthesis systems, such as shoulder prosthesis systems and ankle prosthesis systems.

It should be understood that the modular prosthesis kits of the present invention may include components of different sizes to accommodate the needs of different patient bone sizes.

It will be noted that alternative embodiments of each of the systems of the present disclosure may not include all of the features described yet still benefit from at least some of the advantages of such features. Those of ordinary skill in the art may readily devise their own implementations of a system that incorporates one or more of the features of the present disclosure and fall within the spirit and scope of the invention as defined by the appended claims.

I claim:

1. A sleeve for use in a prosthetic joint system, the sleeve comprising:
    first and second ends, an axial length between the first and second ends, a terraced portion, a fin and an inner wall defining a channel extending between the first and second ends, the channel having a central longitudinal axis;
    the terraced portion including a plurality of adjacent terraces, each terrace having an outer edge around its perimeter, the outer edge of each terrace lying in a plane substantially perpendicular to the central longitudinal axis of the channel; and
    the fin including a pair of outer surfaces spaced from each other at a first distance nearest the first end of the sleeve and a second smaller distance nearest the second end of the sleeve to define a wedge shape;
    wherein:
    the outer surfaces of the fin are continuous and non-terraced;
    the fin has a fin edge connecting the outer surfaces of the fin, the fin edge being spaced from the terraced portion of the sleeve;
    the planes of the outer edges of the terraces are substantially perpendicular to a plane through the fin edge;
    the planes of the outer edges of a plurality of the terraces extend through the fin edge;
    the fin edge tapers toward the central longitudinal axis of the channel so that a first distance between the central longitudinal axis and the fin edge nearest the second end of the sleeve is less than a second greater distance between the central longitudinal axis and the fin edge nearest the first end of the sleeve; and
    the outer surfaces of the fin taper toward the fin edge and toward the second end of the sleeve.

2. A sleeve for use in a prosthetic joint system, the sleeve comprising:
    first and second ends, an axial length between the first and second ends, a terraced portion, a fin and an inner wall defining a channel extending between the first and second ends, the channel having a central longitudinal axis;

the terraced portion including a plurality of adjacent terraces, each terrace having an outer edge around its perimeter, the outer edge of each terrace lying in a plane substantially perpendicular to the central longitudinal axis of the channel; and the fin including a pair of outer surfaces spaced from each other at a first distance nearest the first end of the sleeve and a second smaller distance nearest the second end of the sleeve to define a wedge shape;

wherein:

the outer surfaces of the fin are continuous and non-terraced;

the fin has a fin edge connecting the outer surfaces of the fin, the fin edge being spaced from the terraced portion of the sleeve;

the fin edge tapers toward the central longitudinal axis of the channel so that a first distance between the central longitudinal axis and the fin edge nearest the second end of the sleeve is less than a second greater distance between the central longitudinal axis and the fin edge nearest the first end of the sleeve; and the outer surfaces of the fin taper toward the fin edge and toward the second end of the sleeve and are concavely curved.

3. A knee prosthesis system including a femoral component with condylar surfaces, a tibial component with condylar surfaces to articulate with the condylar surfaces of the femoral component, a stem extension and a sleeve, the sleeve comprising:

first and second ends, an axial length between the first and second ends, a terraced portion, a fin and an inner wall defining a channel extending between the first and second ends, the channel having a central longitudinal axis;

the terraced portion including a plurality of adjacent terraces, each terrace having an outer edge around its perimeter, the outer edge of each terrace lying in a plane substantially perpendicular to the central longitudinal axis of the channel; and the fin including a pair of outer surfaces spaced from each other at a first distance nearest the first end of the sleeve and a second smaller distance nearest the second end of the sleeve to define a wedge shape, wherein the outer surfaces of the fin are continuous and non-terraced and meet along a fin edge;

wherein the fin edge intersects the planes of the outer edges of a plurality of the terraces; and wherein the sleeve is connected to the stem extension and to one of the femoral component and the tibial component connected by complementary locking tapers.

4. A modular knee prosthesis kit comprising:

a femoral component with condylar surfaces;

a tibial component with condylar surfaces to articulate with the condylar surfaces of the femoral component;

a sleeve comprising first and second ends, a central portion, a terraced side wing, a fin, an inner wall defining a channel extending from the first end to the second end, the channel having a central longitudinal axis and tapering from the first end toward the second end, the inner wall having edges defining a circular opening at the first end and a circular opening at the second end, the channel and circular openings being in the central portion of the sleeve;

wherein:

the terraced side wing includes a plurality of adjacent terraces, each terrace having an outer edge around its perimeter, the outer edge of each terrace lying in a plane substantially perpendicular to the central longitudinal axis of the channel;

the fin includes a pair of outer surfaces extending outward from the central portion of the sleeve, the outer surfaces being spaced from each other a first distance nearest the first end of the sleeve and a second smaller distance nearest the second end of the sleeve to define a wedge-shape, wherein the outer surfaces of the fin are continuous and non-terraced;

the fin has a fin edge connecting the outer surfaces of the fin, the fin edge having a length lying in a fin edge plane; and the planes of the outer edges of the terraces are substantially perpendicular to the fin edge plane.

5. The modular knee prosthesis kit of claim 4 wherein the outer surfaces of the fin meet the central portion of the sleeve at junctions and wherein the fin edge is spaced from the junctions of the outer surfaces of the fin and the central portion of the sleeve.

6. The modular knee prosthesis kit of claim 5 wherein the outer surfaces of the fin taper toward the fin edge.

7. The modular knee prosthesis kit of claim 6 wherein the outer surfaces of the fin taper toward the second end of the sleeve.

8. The modular knee prosthesis kit of claim 4 wherein the outer surfaces of the fin taper toward the second end of the sleeve.

9. The modular knee prosthesis kit of claim 4 wherein the central portion of the sleeve has an outer surface that includes terraced and non-terraced portions.

10. The modular knee prosthesis kit of claim 4 wherein:

the tibial component comprises a tibial tray having a stem and a tibial insert carried by the tibial tray; and the sleeve defines a tibial sleeve, the tibial sleeve and the stem being sized and shaped so that the tibial sleeve is mountable on the stem with the stem extending through the channel of the tibial sleeve and frictionally locked to the tibial sleeve.

11. The modular knee prosthesis kit of claim 4 wherein:

the kit further includes a femoral adapter mountable to the femoral component; and the sleeve defines a femoral sleeve, the femoral sleeve and the femoral adapter being sized and shaped so that the femoral sleeve is mountable on the adapter with the adapter extending through the channel of the femoral sleeve and frictionally locked to the femoral sleeve.

12. A modular knee prosthesis kit comprising:

a femoral component with condylar surfaces;

a tibial component with condylar surfaces to articulate with the condylar surfaces of the femoral component;

a sleeve comprising first and second ends, a central portion, a terraced side wing, a fin, an inner wall defining a channel extending from the first end to the second end, the channel having a central longitudinal axis and tapering from the first end toward the second end, the inner wall having edges defining a circular opening at the first end and a circular opening at the second end, the channel and circular openings being in the central portion of the sleeve;

wherein:

the terraced side wing includes a plurality of adjacent terraces, each terrace having an outer edge around its perimeter, the outer edge of each terrace lying in a plane substantially perpendicular to the central longitudinal axis of the channel;

the fin includes a pair of outer surfaces extending outward from the central portion of the sleeve, the outer surfaces being spaced from each other a first distance nearest the first end of the sleeve and a second smaller distance nearest the second end of the sleeve to define a wedge-shape, wherein the outer surfaces of the fin are continuous and non-terraced; and the outer surfaces of the fin taper toward the second end of the sleeve and are concavely curved.

13. A modular knee prosthesis kit comprising:

a femoral component with condylar surfaces;

a tibial component with condylar surfaces to articulate with the condylar surfaces of the femoral component;

a sleeve comprising first and second ends, a central portion, a terraced side wing, a fin, an inner wall defining a channel extending from the first end to the second end, the channel having a central longitudinal axis and tapering from the first end toward the second end, the inner wall having edges defining a circular opening at the first end and a circular opening at the second end, the channel and circular openings being in the central portion of the sleeve;

wherein:

the terraced side wing includes a plurality of adjacent terraces, each terrace having an outer edge around its perimeter, the outer edge of each terrace lying in a plane substantially perpendicular to the central longitudinal axis of the channel;

the fin includes a pair of outer surfaces extending outward from the central portion of the sleeve, the outer surfaces being spaced from each other a first distance nearest the first end of the sleeve and a second smaller distance nearest the second end of the sleeve to define a wedge-shape, wherein the outer surfaces of the fin are continuous and non-terraced;

the fin has a fin edge connecting the outer surfaces of the fin;

the planes of the outer edges of the terraces are substantially perpendicular to a plane through the fin edge;

the outer surfaces of the fin meet the central portion of the sleeve at junctions;

the fin edge is spaced from the junctions of the outer surfaces of the fin and the central portion of the sleeve; and the fin edge is spaced from the central longitudinal axis of the channel of the sleeve at varying distances and the fin edge tapers toward the central longitudinal axis of the channel of the sleeve so that a smallest of the distances between the central longitudinal axis and the fin edge is nearest the second end of the sleeve and a greatest of the distances between the central longitudinal axis and the fin edge is nearest the first end of the sleeve.

14. A modular knee prosthesis kit comprising:

a femoral component with condylar surfaces;

a tibial component with condylar surfaces to articulate with the condylar surfaces of the femoral component;

a sleeve comprising first and second ends, a central portion, a terraced side wing, a fin, an inner wall defining a channel extending from the first end to the second end, the channel having a central longitudinal axis and tapering from the first end toward the second end, the inner wall having edges defining a circular opening at the first end and a circular opening at the second end, the channel and circular openings being in the central portion of the sleeve;

wherein:

the terraced side wing includes a plurality of adjacent terraces, each terrace having an outer edge around its perimeter, the outer edge of each terrace lying in a plane substantially perpendicular to the central longitudinal axis of the channel;

the fin includes a pair of outer surfaces extending outward from the central portion of the sleeve, the outer surfaces being spaced from each other a first distance nearest the first end of the sleeve and a second smaller distance nearest the second end of the sleeve to define a wedge-shape, wherein the outer surfaces of the fin are continuous and non-terraced;

the fin has a fin edge connecting the outer surfaces of the fin;

the planes of the outer edges of the terraces are substantially perpendicular to a plane through the fin edge;

the outer surfaces of the fin meet the central portion of the sleeve at junctions;

the fin edge is spaced from the junctions of the outer surfaces of the fin and the central portion of the sleeve;

the outer surfaces of the fin taper toward the fin edge;

the outer surfaces of the fin taper toward the second end of the sleeve; and the fin edge is spaced from the central longitudinal axis of the channel of the sleeve at varying distances and the fin edge tapers toward the central longitudinal axis of the channel of the sleeve so that a smallest of the distances between the central longitudinal axis and the fin edge is nearest the second end of the sleeve and a greatest of the distances between the central longitudinal axis and the fin edge is nearest the first end of the sleeve.

* * * * *